United States Patent [19]

Rosenberg

[11] Patent Number: 5,062,796
[45] Date of Patent: Nov. 5, 1991

[54] DENTAL HANDPIECE

[76] Inventor: Neil A. Rosenberg, 10 Hussey Farm Rd., Nantucket, Mass. 02554

[21] Appl. No.: 553,382

[22] Filed: Jul. 17, 1990

[51] Int. Cl.$^5$ .................. A61C 1/10; A61C 17/02; A61C 3/02; A61C 1/02; A61C 3/06; A61G 17/02
[52] U.S. Cl. .................................. 433/82; 433/80; 433/88; 433/103; 433/125
[58] Field of Search .................. 433/80, 82, 83, 84, 433/85, 88, 103, 125

[56] References Cited

U.S. PATENT DOCUMENTS

| | | | |
|---|---|---|---|
| 2,400,912 | 5/1946 | Britt et al. | 433/82 |
| 2,738,528 | 3/1956 | Fridge, Sr. | 433/82 |
| 3,389,468 | 12/1964 | Lewis et al. | 433/80 |
| 3,411,210 | 12/1958 | Staunt | 433/82 |
| 3,987,550 | 10/1976 | Danne et al. | 433/84 |
| 4,220,446 | 9/1980 | Walker | 433/85 |
| 4,315,741 | 2/1982 | Reichl | 433/82 |
| 4,318,695 | 3/1982 | Lieb et al. | 433/132 |
| 4,696,644 | 9/1987 | Goof | 433/88 |

Primary Examiner—John J. Wilson
Assistant Examiner—Cindy A. Cherichetti
Attorney, Agent, or Firm—Burns, Doane, Swecker & Mathis

[57] ABSTRACT

A dental handpiece for rotating a dental cleaning tool includes a casing in which there is mounted a drive shaft that is operably connected to the cleaning tool. A rotor is affixed to the drive shaft and is driven by compressed air fed to the casing. The drive shaft is hollow and communicates with a reservoir situated within the casing. The reservoir contains a refillable supply of dental paste. Pressurized air is fed to the reservoir to push paste through the hollow drive shaft and into the dental cleaning tool. The interior of the drive shaft includes a helical screw which aids in feeding the paste toward the cleaning tool.

16 Claims, 1 Drawing Sheet

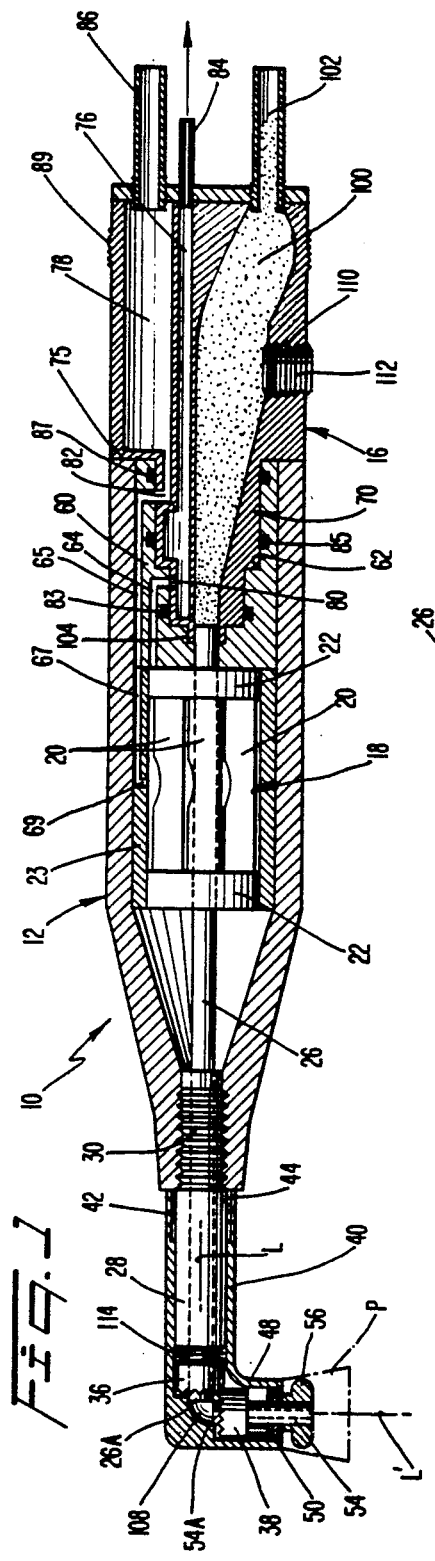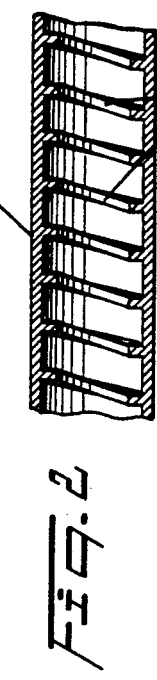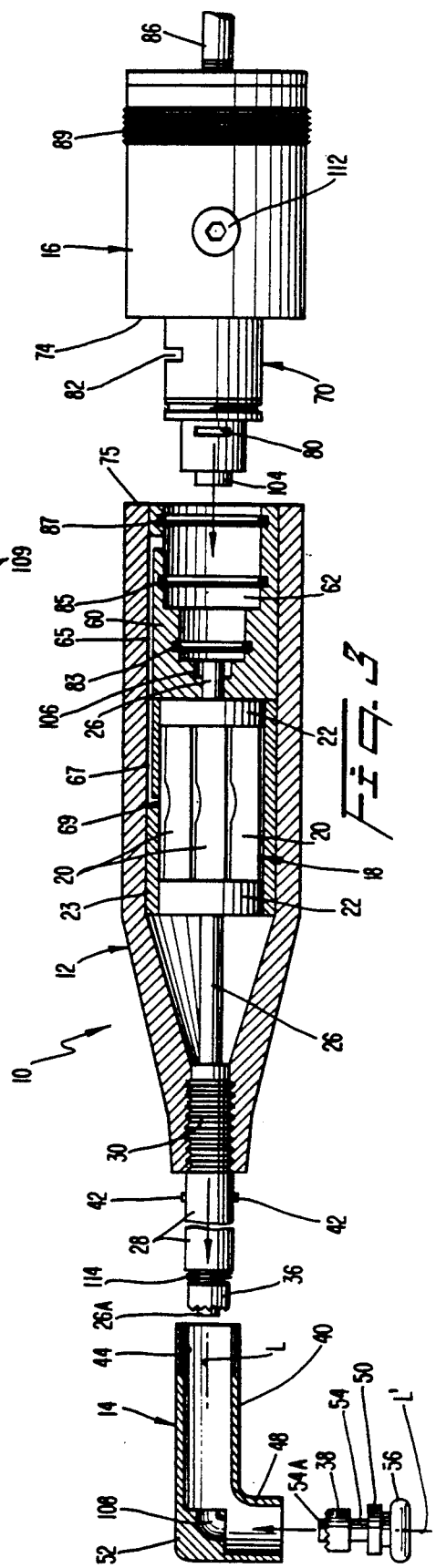

DENTAL HANDPIECE

BACKGROUND OF THE INVENTION

The present invention relates to dental equipment, and especially to a dental handpiece which carries a supply of dental paste to be delivered to a patient's mouth in conjunction with the performance of a teeth cleaning operation. The invention also relates to a method of cleaning teeth.

In the performance of teeth cleaning operations, a prophy cup is rotated at the end of a handpiece to scrub the teeth with a paste. It is necessary to frequently transfer the prophy cup from the patient's mouth to a paste container in order to refill the prophy cup with paste. Such a practice interrupts and prolongs the cleaning operation.

In an effort to alleviate that shortcoming, it has been previously proposed to integrate a paste supply with the dental handpiece and provide mechanical power for delivering the paste to the patient's mouth, e.g., see U.S. Pat. Nos. 2,400,912; 2,738,528; 3,987,550; and 4,220,446.

For example, U.S. Pat. No. 2,400,912 discloses a handpiece possessing an internal paste chamber which communicates with a prophy cup by means of an external flexible conduit. A linearly movable plunger disposed within the paste chamber is displaceable by a mechanical take-off from the drive train which rotates the prophy cup. By displacing the plunger, paste from the chamber is forced through the conduit and into the prophy cup.

In U.S. Pat. No. 3,987,550 and U.S. Pat. No. 4,220,446 dental handpieces are disclosed wherein paste is stored within an external container secured to the handpiece. A plunger extends into the container and is actuated by pressurized fluid such as air or water, in order to dispense the paste. The pressurized fluid is admitted to the plunger by means of a hand or foot actuated valve.

U.S. Pat. No. 2,738,528 discloses a handpiece in which a squeezable paste container is mounted on the exterior of the handpiece casing. An external conduit leads from the container to the prophy cup. By manually squeezing the container, paste is able to be delivered to the prophy cup.

It will be appreciated that the handpieces disclosed in the aforementioned patents involve certain drawbacks. For example, the provision of external containers and/or conduits makes the handpiece cumbersome and more difficult to maneuver about a patient's mouth. Also, the need to provide auxiliary means of power to eject the paste adds expense and complexity to the system, as does the need to provide extra components such as plungers and hand or foot controls for example. It is also inconvenient for the operator to have to manipulate a foot or hand control in order to dispense the paste.

SUMMARY OF THE INVENTION

The present invention relates to a dental handpiece comprising a casing having front and rear ends situated and defining a front-to-rear extending axis. A rotatably driven output member is disposed at the front end of the casing and is adapted to removably carry a rotary dental cleaning tool. A hollow drive shaft is mounted in the casing for rotation about the front-to-rear extending axis and is operably connected to the output member to drive the latter. An air driven rotor is connected to the hollow drive shaft for transmitting rotary motion thereto. A reservoir situated within the casing communicates with the hollow drive shaft for introducing a flowable cleaning agent thereinto. Pressurized air is supplied to the rotor for rotating the hollow drive shaft and the output member. Pressurized air is also supplied to the hollow drive shaft for forcing cleaning agent through the hollow drive shaft toward the output member.

Preferably, the output member comprises a driven shaft which is rotatable about an output axis extending at an angle relative to the axis of the hollow drive shaft.

Preferably, the hollow drive shaft includes an internal helical screw arranged to be rotated with the hollow drive shaft for forcing cleaning agent through the output member.

BRIEF DESCRIPTION OF THE DRAWINGS

The objects and advantages of the invention will become apparent from the following detailed description of a preferred embodiment thereof in connection with the accompanying drawings in which like numerals designate like elements, and in which:

FIG. 1 is a longitudinal sectional view taken through a dental handpiece according to the present invention;

FIG. 2 is a fragmentary longitudinal sectional view of a drive shaft portion of the dental handpiece, depicting an internal screw thereof; and FIG. 3 is an exploded longitudinal sectional view taken through the handpiece.

DETAILED DESCRIPTION OF A PREFERRED EMBODIMENT OF THE INVENTION

A dental handpiece 10 according to the present invention is of the type wherein a drive shaft is driven by an air-powered rotor for rotating a dental tool, such as a prophy cup, carried by the handpiece.

The handpiece 10 comprises a casing formed by a main housing 12, a head 14 removably attached to a front end of the housing 12, and a connector 16 removably attached to a rear end of the housing 12.

Disposed within the main housing 12 is a conventional rotor assembly 18 comprised of a hub from which a plurality of rotor blades 20 project radially, and a pair of end plates 22. The end plates contain bearings (not shown) which rotatably support the ends of the rotor for rotation about an axis coinciding with the longitudinal axis L of the casing. The end plates are contained within a cylinder 23 which surrounds the rotor. Such a rotor assembly is conventional and can be purchased as a unit.

Extending coaxially through the rotor 18 is a drive shaft 26 which is affixed to the rotor by a friction fit or heat shrink fit, for example, for rotation therewith. The drive shaft could, for example, be mounted by a splined connection to the rotor hub whereby rotation of the rotor is transmitted to the drive shaft. A forward end of the drive shaft extends through a sleeve-type bearing 28 which is seated within the main housing, e.g., by means of a screw thread attachment 30.

Affixed adjacent a front end of the drive shaft 26 is a drive gear 36 which meshes with a driven gear 38, the latter being mounted in the head 14 for rotation about an axis L' oriented at an angle, e.g., 90°, relative to the axis of rotation L of the drive shaft 26.

The head 24 includes a first tubular portion 40 which telescopingly receives the bearing 28 and is attached thereto by a bayonet coupling formed by pins 42 on the bearing which are received in slots 44 formed in an inner surface of the head. Alternatively, a threaded coupling could be employed. The head 14 also includes a second tubular portion 48 which carries a bearing 50 for rotatably supporting a driven shaft 54 on which the driven gear 38 is fixed. The bearing can be secured in the tubular portion 48 in any suitable fashion, such as by a conventional retaining ring. An elbow portion 52 of the head interconnects the tubular portions 40, 48. A conventional coupling flange 56 is disposed at the lower end of the driven shaft 54 for mounting a conventional prophy cup P.

Mounted in the rear end of the housing 12 is an insert 60 which forms a rearwardly open, stepped socket 62. The insert includes a pair of air conducting passages 64, 65 (see FIGS. 1 and 3) leading to and from the rotor assembly 18. The passage 65 communicates with a channel 67 formed in the outer surface of the cylinder 23 (see FIG. 3), and that channel 67 communicates with a port 69 formed in the cylinder 23 to direct air circumferentially against the rotor blades in conventional fashion.

The connector 16 possesses a stepped tongue portion 70 which slidably mates with the socket 62. The tongue portion 70 projects forwardly from a rear portion 72 of the connector to form a radial shoulder 74 therewith. That shoulder 74 abuts a shoulder 75 at the rear end of the housing 12. The connector includes air ingress and air egress passages 76, 78 (see FIG. 1) which terminate at openings 80, 82, respectively, in the tongue portion 70. Those openings 80, 82 communicate with the air inlet and air outlet passages 64, 65, respectively, in the housing 12 to conduct air to and from the rotor assembly in conventional fashion to rotate the rotor 20, drive shaft 26, driven shaft 54, and prophy cup P. O-ring seals 83, 85, 87 are carried by the tongue 70 to isolate the various air passages from one another.

Air is supplied to the passages 76, 78 from a conventional air supply hose (not shown) which is releasably connectable to threads 89 on the rear end of the connector 16 such that air conduits in the hose are joined to air fittings 84, 86 attached to the rear end of the connector 16.

The thus far-described apparatus is generally conventional In accordance with the present invention, however, the handpiece 10 is provided with means for supplying the prophy cup with a dental paste. As will be explained, hereinafter the paste is contained within the connector 16 and is advanced to the prophy cup through the drive shaft by forces generated by the same compressed air source which powers the rotor 18.

In that regard, the connector includes a paste reservoir 100 which has at its rear end an air inlet fitting 102. The fitting 102 connects to an air conduit in the air supply hose (not shown). An outlet tube 104 of the reservoir projects centrally from a front end of the tongue 70 and is sized to be received in a center bore 106 of the socket 62. The drive shaft 26 is hollow and is arranged so that the hollow interior thereof communicates with the bore 106.

A front end 26A of the drive shaft projects forwardly beyond the drive gear 36 and is sized to be received in the inlet end of a transition passage 108 formed in the elbow portion 52 of the head 14. An end 54A of the driven shaft 54 also projects beyond the driven gear 38 and is sized to be received in the outlet end of the transition passage 108. O-ring seals can be provided on those projecting ends 24A, 54A of the drive and driven shafts 26, 54 to create a seal when those projecting ends are inserted into the transition passage 108.

It will be appreciated that when pressurized air is injected into the paste reservoir 100 through the air fitting 102, paste is forced to travel through the drive shaft 26, the transition passage 108, and the driven shaft 54 and into the interior of the prophy cup P. This is achieved without encumbering the outer periphery of the handpiece with extra canisters or conduits, and without the need to furnish an extra energy source, since advantage is taken of the compressed air source used to drive the rotor.

The paste employed will possess a consistency enabling the paste to flow smoothly through the passages. In the event that extra pushing force on the paste would be beneficial, that could be achieved by providing the interior of the drive shaft 26 and/or driven shaft 54 with a screw thread 109 (see FIG. 2). Thus, the rotation of those shafts produces a mechanical advancement of the paste which augments the force of the pressurized air acting directly against the paste. While it is conceivable that the screw drive presented by the shafts 26, 54 could be used to advance the paste in lieu of pressurized air from the fitting 102 by extending the screw into the reservoir 100, it is anticipated that the screw drive would only be used to augment the pushing force of the pressurized air.

The operator is able to terminate the flow of paste by keeping the open end of the prophy cup P pressed against the patient's teeth. As a result, a back-pressure develops within the drive and driven shafts to retain the paste in place. By lifting the prophy cup from the teeth, flow of the paste resumes. Therefore, there occurs a continuous forward bias on the paste during the cleaning operation, but the paste flow is easily controlled. There is no need to provide separate hand or foot actuated valves for regulating the paste flow.

The connector 16 includes a lateral opening 110 which communicates with the reservoir 100. The opening receives a removable closure, e.g., a threaded cap 112. By removing the cap, the reservoir can be refilled with paste.

The drive gear 36 is preferably mounted on the drive shaft 26 by means of a spline connection with permits the drive gear 36 to move longitudinally relative to that shaft when the head 14 is attached to the housing 12. A spring 114 biases the drive gear 36 forwardly but yields to permit rearward displacement of the drive gear in order to ensure proper meshing between the gears 36, 38.

In accordance with the present invention a paste supply is integrated with the handpiece without the use of exterior containers or conduits which would unduly enlarge the handpiece and make it more awkward to use. No additional power source is required, since the source of compressed air for driving the rotor is used. The number of mechanical parts for pressuring the paste is minimized. There is no need to provide a piston to push the paste; pushing is accomplished by compressed air and/or the screw thread of the drive shaft. There is no need to provide hand or foot controlled valves since the flow of paste can be stopped by pressing the prophy cup against the patient's teeth, and started by lifting the prophy cup off the teeth.

Although the present invention has been described in connection with a preferred embodiment thereof, it will be appreciated by those skilled in the art that additions, substitutions, modifications, and deletions, not specially described may be made without departing from the spirit and scope of the invention as defined in the appended claims.

What is claimed is:

1. A dental handpiece comprising:
   a casing having front and rear ends and defining a front-to-rear extending axis,
   a rotatably driven output member disposed at said front end of said casing and adapted to removably carry a rotary dental tool,
   hollow drive shaft means mounted in said casing for rotation about said front-to-rear extending axis and being operably connected to said output member to drive the latter, said hollow drive shaft means defining an internal conduit,
   an air-driven rotor connected to said hollow drive shaft means for transmitting rotary motion thereto,
   means situated within said casing and communicating with said hollow drive shaft means for introducing a flowable cleaning agent into said internal conduit defined by said hollow drive shaft means,
   means for supplying pressurized air to said rotor for pneumatically rotating said hollow drive shaft means and said output member, and for supplying pressurized air into said internal conduit defined by said hollow drive shaft means for pneumatically forcing cleaning agent through said internal conduit toward said output member.

2. A dental handpiece according to claim 1, wherein said output member is rotatable about an output axis extending at an angle relative to said front-to-rear extending axis.

3. A dental handpiece according to claim 2 including gear means for transmitting rotary motion from said hollow drive shaft means to said output member.

4. A dental handpiece according to claim 1, wherein said casing includes a housing in which said hollow drive shaft means is disposed, and a connector removably attached at a rear end of said housing, said means for introducing a flowable cleaning agent comprising a reservoir disposed in said connector.

5. A dental handpiece according to claim 4, wherein said connector includes a closable opening communicating with said reservoir for introducing cleaning agent thereto.

6. A dental handpiece according to claim 4, wherein said connector includes air passage means for conducting pressurized air to said rotor and said reservoir.

7. A dental handpiece according to claim 4, wherein said casing includes a head removably attached to a front end of said housing, said output member comprising an output shaft disposed in said head and rotatable about an output axis oriented at an angle relative to said front-to-rear axis, said output shaft including means for connection with a rotary dental tool.

8. A dental handpiece according to claim 1, wherein said hollow drive shaft means includes internal screw means disposed within said internal conduit and arranged to be rotated with said hollow drive shaft means for mechanically forcing cleaning agent toward said output member.

9. A dental handpiece comprising:
   a casing having front and rear ends and defining a front-to-rear extending axis,
   a rotatably driven output member disposed at said front end of said casing and adapted to removably carry a rotary dental tool,
   hollow drive shaft means mounted in said casing for rotation about said front-to-rear axis and being operably connected to said output member to drive the latter, said hollow drive shaft means defining an internal conduit including internal helical screw means arranged to be rotated with said hollow screw shaft means,
   a rotor connected to said drive shaft,
   a reservoir situated within said casing and communicating with said hollow drive shaft means for introducing a flowable cleaning agent into said internal conduit, and
   means for supplying pressurized air to said rotor for pneumatically rotating said drive shaft and said internal screw means and for supplying pressurized air into said internal conduit for pneumatically forcing cleaning agent through said toward said output member by the combined forces of said internal screw means and said pressurized air.

10. A dental handpiece comprising:
    a casing having front and rear ends and defining a front-to-rear extending axis,
    hollow drive shaft means mounted in said casing for rotation about said front-to-rear extending axis, said hollow drive shaft means defining an internal conduit,
    a hollow output member disposed in said casing and rotatable about an output axis oriented at an angle relative to said front-to-rear axis, said output member adapted to be connected to a rotary dental tool,
    a first gear operably coupled to a front end of said hollow drive shaft means,
    a second gear operably coupled to said output member and to said first gear for transmitting rotary motion from said hollow drive shaft means to said hollow output member,
    passage means in said casing for communicating said internal conduit of said hollow drive shaft means with a hollow interior of said hollow output member,
    means in said casing communicating with said hollow drive shaft means for introducing a flowable cleaning agent into said internal conduit,
    drive means for rotating said hollow drive shaft means to drive said hollow output member, said drive means comprising an air driven rotor operably coupled to said hollow drive shaft means, and means for supplying pressurized air to said rotor for pneumatically rotating said rotor and said hollow drive shaft means, and
    means for forcing cleaning agent forwardly through said internal conduit of said hollow drive shaft means and through said hollow interior of said hollow output member, said means for forcing cleaning agent comprising means for supplying pressurized air into said internal conduit of said hollow drive shaft means.

11. A dental handpiece according to claim 10, wherein said drive means comprises an air driven rotor operably coupled to said hollow drive shaft means, and means for supplying pressurized air to said rotor for rotating said rotor and said hollow drive shaft means, said means for forcing cleaning agent comprising means for supplying pressurized air to said hollow interior of said hollow drive shaft means.

12. A dental handpiece according to claim 11, wherein said hollow interior of said hollow drive shaft means includes internal screw means which rotates with said hollow drive shaft means to aid in forcing cleaning agent forwardly within said hollow interior.

13. A dental handpiece according to claim 10, wherein said means for forcing cleaning agent includes internal screw means disposed in said hollow interior of said hollow drive shaft means so as to be rotatable with said hollow drive shaft means.

14. A method of cleaning teeth with a dental handpiece comprising the steps of:
applying against a patient's teeth a rotating cleaning tool which is attached to said handpiece,
supplying pressurized air to said handpiece and into direct engagement with flowable cleaning agent contained in said handpiece continuously during said applying step to continuously urge cleaning agent toward said cleaning tool,
blocking the flow of cleaning agent into said cleaning tool by pressing said cleaning tool against a tooth, and
allowing cleaning agent to flow into said cleaning tool by raising said cleaning tool from the tooth.

15. A method according to claim 14, wherein said cleaning agent is conducted within passage means disposed entirely inside of said handpiece.

16. A method according to claim 15, wherein pressurized air is also supplied to a rotor operably connected to a drive shaft which drives said cleaning tool, said drive shaft including internal screw thread means for urging cleaning agent toward said cleaning tool.

* * * * *